United States Patent
Nordt, III et al.

(10) Patent No.: US 7,618,386 B2
(45) Date of Patent: Nov. 17, 2009

(54) TWO-COMPONENT COMPRESSION COLLAR CLAMP FOR ARM OR LEG

(75) Inventors: William E. Nordt, III, Charles City, VA (US); Ian D. Kovacevich, Charlotte, NC (US); Kevin J. Dahlquist, Charlotte, NC (US); Tom J. Philpott, Charlotte, NC (US)

(73) Assignee: Nordt Development Co., LLC, Charles City, VA (US)

( * ) Notice: Subject to any disclaimer, the term of this patent is extended or adjusted under 35 U.S.C. 154(b) by 388 days.

(21) Appl. No.: 11/187,590

(22) Filed: Jul. 22, 2005

(65) Prior Publication Data

US 2006/0020237 A1    Jan. 26, 2006

Related U.S. Application Data

(63) Continuation-in-part of application No. 29/209,971, filed on Jul. 22, 2004, now Pat. No. Des. 519,637, and a continuation-in-part of application No. 29/209,987, filed on Jul. 22, 2004, now Pat. No. Des. 521,644.

(60) Provisional application No. 60/590,940, filed on Jul. 22, 2004, provisional application No. 60/590,947, filed on Jul. 22, 2004.

(51) Int. Cl.
*A61F 5/00* (2006.01)
*A61F 13/00* (2006.01)

(52) U.S. Cl. .................. 602/20; 602/5; 602/62

(58) Field of Classification Search .......... 602/5, 602/20, 23, 26, 27, 19; 128/877–879; 2/311, 2/312; 601/62; 606/201, 202, 204
See application file for complete search history.

(56) References Cited

U.S. PATENT DOCUMENTS

| 101,743 | A |   | 8/1870 | King |   |
|---|---|---|---|---|---|
| 667,768 | A |   | 2/1901 | De Puy |   |
| 839,553 | A | * | 12/1906 | Cohn | 2/311 |
| 1,227,700 | A |   | 5/1917 | Tucker |   |
| 1,233,112 | A |   | 7/1917 | Nylander |   |

(Continued)

FOREIGN PATENT DOCUMENTS

WO    WO 9106265 A1 *  5/1991

(Continued)

*Primary Examiner*—Kim M Lewis
(74) *Attorney, Agent, or Firm*—Tillman Wright, PLLC; Chad D. Tillman; Jeremy C. Doerre

(57) ABSTRACT

An apparatus for disposition on appendage, such as an arm or leg, is capable of encircling and applying opposing forces selectively thereto. A C-shaped component receives one side of the appendage, a second C-shaped component receives the other side of the appendage, and a tensioning system draws the two components together for selective application of pressure to the appendage. Outriggers and pressure applicators may be used to apply pressure to extended areas of the appendage that otherwise would not be engaged by the C-shaped components. Side-to-side tissue compression thereby is provided for deflection of muscle forces, functional shortening of muscle length, and the maintenance of neurovascular channels. Circumferential forces may be minimized based on semirigid characteristics of the components. Elbow and shoulder braces apply side-to-side tissue compression to arms.

38 Claims, 7 Drawing Sheets

U.S. PATENT DOCUMENTS

| | | | |
|---|---|---|---|
| 1,298,529 A | 3/1919 | Maddox | |
| 2,312,523 A | 3/1943 | Corbett | |
| 2,357,323 A | 4/1944 | Goldberg | |
| 2,570,662 A * | 10/1951 | Gray | 70/16 |
| 2,692,594 A | 10/1954 | Kelly | |
| 3,419,003 A | 12/1968 | Krauss et al. | |
| 3,551,912 A | 1/1971 | Viglione | |
| 3,788,307 A | 1/1974 | Kistner | |
| 4,048,991 A | 9/1977 | Marx | |
| 4,168,063 A | 9/1979 | Rowland | |
| 4,240,414 A | 12/1980 | Theisler | |
| 4,269,181 A | 5/1981 | Delannoy | |
| 4,287,885 A | 9/1981 | Applegate | |
| 4,372,298 A | 2/1983 | Lerman | |
| 4,378,009 A | 3/1983 | Rowley | |
| 4,382,439 A | 5/1983 | Shen | |
| 4,446,858 A | 5/1984 | Verter | |
| 4,466,428 A | 8/1984 | McCoy | |
| 4,644,939 A | 2/1987 | Coleman | |
| 4,660,550 A | 4/1987 | Bodine | |
| 4,677,971 A | 7/1987 | Lindemann | |
| 4,765,319 A | 8/1988 | Finnieston | |
| 4,768,502 A | 9/1988 | Lee | |
| 4,805,606 A | 2/1989 | McDavid | |
| 4,856,501 A | 8/1989 | Castillo | |
| 4,862,878 A | 9/1989 | Davison et al. | |
| 4,873,968 A | 10/1989 | Finnieston et al. | |
| 4,881,533 A | 11/1989 | Teurlings | |
| 4,928,678 A | 5/1990 | Grim | |
| 4,940,044 A | 7/1990 | Castillo | |
| 4,941,460 A | 7/1990 | Working | |
| 4,971,041 A | 11/1990 | Millikan et al. | |
| 5,016,621 A | 5/1991 | Bender | |
| 5,018,513 A | 5/1991 | Charles | |
| D318,736 S | 7/1991 | Castillo | |
| 5,036,837 A | 8/1991 | Mitchell et al. | |
| 5,042,177 A * | 8/1991 | Schoch | 36/50.5 |
| 5,086,761 A | 2/1992 | Ingram | |
| 5,091,992 A | 3/1992 | Pusic | |
| 5,134,992 A | 8/1992 | Campbell | |
| 5,188,587 A | 2/1993 | McGuire et al. | |
| 5,205,812 A | 4/1993 | Wasserman | |
| 5,213,094 A | 5/1993 | Bonutti | |
| 5,230,697 A | 7/1993 | Castillo et al. | |
| 5,254,078 A | 10/1993 | Carter et al. | |
| D340,990 S | 11/1993 | Kawamura | |
| 5,267,708 A | 12/1993 | Monson et al. | |
| 5,279,545 A | 1/1994 | Reese, Sr. | |
| 5,295,948 A | 3/1994 | Gray | |
| 5,307,521 A | 5/1994 | Davis | |
| 5,334,135 A | 8/1994 | Grim et al. | |
| 5,358,471 A | 10/1994 | Klotz | |
| 5,368,549 A | 11/1994 | McVicker | |
| 5,372,575 A | 12/1994 | Sebastian | |
| 5,395,304 A | 3/1995 | Tarr et al. | |
| 5,399,154 A | 3/1995 | Kipnis et al. | |
| 5,404,591 A | 4/1995 | Brinnard | |
| 5,409,451 A | 4/1995 | Daneman | |
| D358,215 S | 5/1995 | Reed | |
| 5,415,623 A | 5/1995 | Cherubini | |
| 5,417,646 A | 5/1995 | Gauvry | |
| 5,425,702 A | 6/1995 | Carn et al. | |
| 5,437,620 A | 8/1995 | Shelly | |
| 5,441,015 A * | 8/1995 | Farley | 602/28 |
| 5,450,625 A | 9/1995 | Hu | |
| 5,455,969 A | 10/1995 | Pratson et al. | |
| 5,458,565 A | 10/1995 | Tillinghast, III et al. | |
| 5,468,220 A | 11/1995 | Sucher | |
| 5,472,410 A | 12/1995 | Hamersly | |
| 5,472,413 A | 12/1995 | Datty | |
| 5,507,720 A | 4/1996 | Lampropoulos | |
| 5,512,039 A | 4/1996 | White | |
| 5,520,628 A * | 5/1996 | Wehr | 602/27 |
| D370,533 S | 6/1996 | Kilbey | |
| D371,845 S | 7/1996 | Varn | |
| D373,655 S | 9/1996 | Kalvestran et al. | |
| 5,584,799 A | 12/1996 | Gray | |
| 5,599,288 A | 2/1997 | Shirley et al. | |
| 5,621,985 A | 4/1997 | Frost | |
| 5,628,725 A | 5/1997 | Ostergard | |
| 5,637,078 A | 6/1997 | Varn | |
| 5,653,680 A | 8/1997 | Cruz | |
| 5,658,244 A | 8/1997 | Townsend | |
| 5,672,150 A | 9/1997 | Cox | |
| 5,695,452 A | 12/1997 | Grim et al. | |
| D390,961 S | 2/1998 | Walker et al. | |
| 5,713,837 A | 2/1998 | Grim et al. | |
| 5,725,490 A | 3/1998 | Conran | |
| 5,782,785 A | 7/1998 | Herzberg | |
| 5,807,298 A | 9/1998 | Palumbo | |
| 5,810,753 A | 9/1998 | Eberbach | |
| 5,823,981 A | 10/1998 | Grim et al. | |
| 5,836,902 A | 11/1998 | Gray | |
| 5,848,979 A | 12/1998 | Bonutti et al. | |
| 5,857,987 A | 1/1999 | Habermeyer | |
| 5,857,988 A | 1/1999 | Shirley | |
| 5,873,130 A | 2/1999 | Lafferty | |
| 5,891,061 A | 4/1999 | Kaiser | |
| 5,921,243 A | 7/1999 | Shakoor | |
| 5,921,945 A | 7/1999 | Gray | |
| 5,928,172 A | 7/1999 | Gaylord | |
| 5,971,947 A | 10/1999 | McNally et al. | |
| D416,624 S | 11/1999 | Nauert | |
| 6,024,712 A | 2/2000 | Iglesias et al. | |
| 6,048,253 A | 4/2000 | Larsen | |
| 6,066,110 A | 5/2000 | Nauert | |
| 6,071,175 A | 6/2000 | Working, III | |
| 6,102,880 A | 8/2000 | Nelson et al. | |
| 6,106,493 A | 8/2000 | Rozell | |
| 6,120,471 A | 9/2000 | Varn | |
| 6,132,393 A | 10/2000 | Lundberg | |
| D433,756 S | 11/2000 | Castillo | |
| 6,142,965 A | 11/2000 | Mathewson | |
| 6,146,346 A | 11/2000 | Godwin | |
| 6,152,891 A | 11/2000 | Carlson | |
| 6,179,799 B1 | 1/2001 | Doran | |
| 6,223,350 B1 | 5/2001 | McFarlane | |
| 6,253,376 B1 | 7/2001 | Ritter | |
| 6,308,332 B1 | 10/2001 | Tollini | |
| 6,311,337 B1 | 11/2001 | Tollini | |
| 6,322,528 B1 | 11/2001 | Kania | |
| 6,393,610 B1 | 5/2002 | Parks | |
| 6,398,746 B2 | 6/2002 | Bramlage et al. | |
| 6,398,748 B1 | 6/2002 | Wilson | |
| 6,401,245 B1 | 6/2002 | Slautterback | |
| 6,406,450 B1 | 6/2002 | Kowalczyk et al. | |
| 6,425,876 B1 | 7/2002 | Frangi et al. | |
| 6,436,066 B1 | 8/2002 | Lockhart | |
| 6,443,918 B1 | 9/2002 | Wang | |
| 6,478,760 B2 | 11/2002 | Darcey | |
| 6,502,577 B1 | 1/2003 | Bonutti | |
| D473,656 S | 4/2003 | Miros et al. | |
| 6,540,710 B1 | 4/2003 | Cruz | |
| 6,553,572 B2 | 4/2003 | Fiorini et al. | |
| D475,789 S | 6/2003 | McCormick et al. | |
| D477,409 S | 7/2003 | Mills et al. | |
| 6,592,538 B1 | 7/2003 | Hotchkiss et al. | |
| 6,599,263 B1 | 7/2003 | Bonutti et al. | |
| 6,629,598 B2 | 10/2003 | Narula et al. | |
| 6,671,884 B1 | 1/2004 | Griesbach, III et al. | |
| 6,716,185 B1 | 4/2004 | Reiger | |
| 6,719,653 B1 | 4/2004 | Nesbitt | |
| 6,773,410 B2 | 8/2004 | Varn | |
| 6,790,192 B2 | 9/2004 | Robinson | |

| | | |
|---|---|---|
| 6,835,182 B2 | 12/2004 | Darcey |
| 7,118,543 B2 * | 10/2006 | Telles et al. .................. 602/19 |
| 7,490,458 B2 * | 2/2009 | Ford .............................. 54/82 |
| 2002/0052568 A1 | 5/2002 | Houser et al. |
| 2002/0077574 A1 | 6/2002 | Gildersleeve et al. |
| 2002/0094919 A1 | 7/2002 | Rennex et al. |
| 2002/0148461 A1 | 10/2002 | Heinz et al. |
| 2003/0120183 A1 | 6/2003 | Simmons |
| 2003/0171703 A1 | 9/2003 | Grim et al. |
| 2004/0019307 A1 | 1/2004 | Grim et al. |
| 2004/0049291 A1 | 3/2004 | Deharde et al. |
| 2004/0210177 A1 | 10/2004 | Grim et al. |
| 2005/0054960 A1 * | 3/2005 | Telles et al. .................. 602/19 |
| 2005/0165338 A1 | 7/2005 | Iglesias et al. |

FOREIGN PATENT DOCUMENTS

WO    WO 9310727 A1 *   6/1993

* cited by examiner

TWO-COMPONENT COMPRESSION COLLAR CLAMP FOR ARM OR LEG

CROSS-REFERENCE TO RELATED APPLICATIONS

The present application includes four priority documents. The present application is a continuation-in-part nonprovisional utility patent application of, and claims the benefit of priority under 35 U.S.C. §120 to, each of: (1) U.S. design patent application Ser. No. 29/209,971, filed Jul. 22, 2004 now U.S. Pat. No. Des. 519,637, which is incorporated herein by reference; and (2) U.S. design patent application Ser. No. 29/209,987, filed Jul. 22, 2004 now U.S. Pat. No. Des. 521, 644 which is incorporated herein by reference. The present application also is a nonprovisional patent application of, and claims the benefit of priority under 35 U.S.C §119(e) to, each of: (3) U.S. provisional patent application Ser. No. 60/590, 940, filed Jul. 22, 2004, which is incorporated herein by reference; and (4) U.S. provisional patent application Ser. No. 60/590,947, filed Jul. 22, 2004, which is incorporated herein by reference.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

Life expectancies are rising and diverse athletic activities are becoming increasingly available to people of all ages. Accordingly, the number of people suffering current minor injuries, the number of people living with chronic joint ailments, and the number of people facing the possibilities of sports-related injuries are ever increasing.

Many braces for disposition on an arm or leg are available to aid such people. However, most available braces and joint-support accessories are complex, unattractive, and uncomfortable There are braces for preventing joint motion or for maintaining a particular joint position. Typical such braces, having hard-shell or rigid beam components, are not typically conveniently adjusted with regard to forces and resulting pressures applied to an arm or leg and with regard to a comfortable fit. There also are braces for use in supporting active joint motion. These braces generally include binding arrangements that tend to apply circumferential forces to an arm or leg and adversely affect blood flow and circulation.

A demand therefore is growing for one or more braces that improve upon the braces currently available.

SUMMARY OF THE INVENTION

A first aspect of the invention generally relates to an apparatus for disposition on a person's body, such as an arm or leg. More particularly, the first aspect of the invention relates to an apparatus for circumferential disposition on an arm or leg and for selectively applying thereto forces and resulting pressures. According to this aspect, a first partial collar and second partial collar, together preferably completely encircling an arm or leg, are drawn together by a tensioning system such that opposing forces are thereby applied to the arm or leg.

In accordance with this and other aspects, the partial collars generally are C-shaped, and each C-shaped partial collar may comprise arcuate segments, polygonal segments, or both. Furthermore, as used herein, "C-shaped" is intended to encompass both "U-shaped" and other variations and equivalents thereof, including the component shapes of the drawings set forth herein.

In a feature of the first aspect, a tensioning system includes a rotary device and tensioning lines for controllably varying the forces applied to the arm or leg. In one example, rotation of a handle or control knob of the rotary device causes the tensioning lines to retract and the forces of the partial collars engaging the appendage to be increased.

In an exemplary construction related to the first aspect of the invention, end portions of one partial collar are disposed between end portion of the other partial collar and the arm or leg. Optionally within that construction, one of the partial collars has conduits or channels for receiving end portions of the other partial collar.

Partial collars optionally apply pressure to selective areas of an arm or leg in conjunction with, or by way of, pressure applicators. In some variations, pressure applicators generally apply pressure within margins of the partial collars. In other variations, pressure applicators are attached to outriggers that extend beyond margins of the partial collars.

Another aspect of the invention relates to a brace for disposition on an arm or leg. More particularly, an inventive brace includes a first clamping component and a second clamping component that, together, preferably circumferentially surround the arm or leg when the brace worn. Tensional forces draw the clamping components toward one another and thereby apply directionally opposing forces to the arm or leg.

A third aspect of the invention relates to an apparatus for disposition on an arm or leg. More particularly, an inventive apparatus according to this aspect of the invention includes a collar for encircling an appendage. The apparatus further includes a rotary device having a housing, a rotatable control knob, and a line depending from the housing. When the rotatable control knob is rotated, the line is partially drawn into the housing, whereby a force applied to the arm or leg encircled by the apparatus is increased.

Additional aspects of the present invention relate to methods associated with the aforementioned aspects.

BRIEF DESCRIPTION OF THE DRAWINGS

These and other aspects of the invention, as well as one or more embodiments of the present invention, are disclosed with reference to the accompanying drawings which are briefly described below, wherein the same elements are referred to with the same reference numerals, and wherein various elements are not necessarily shown in conformance to any particular absolute or relative scale.

DETAILED DESCRIPTION

Figure 1:
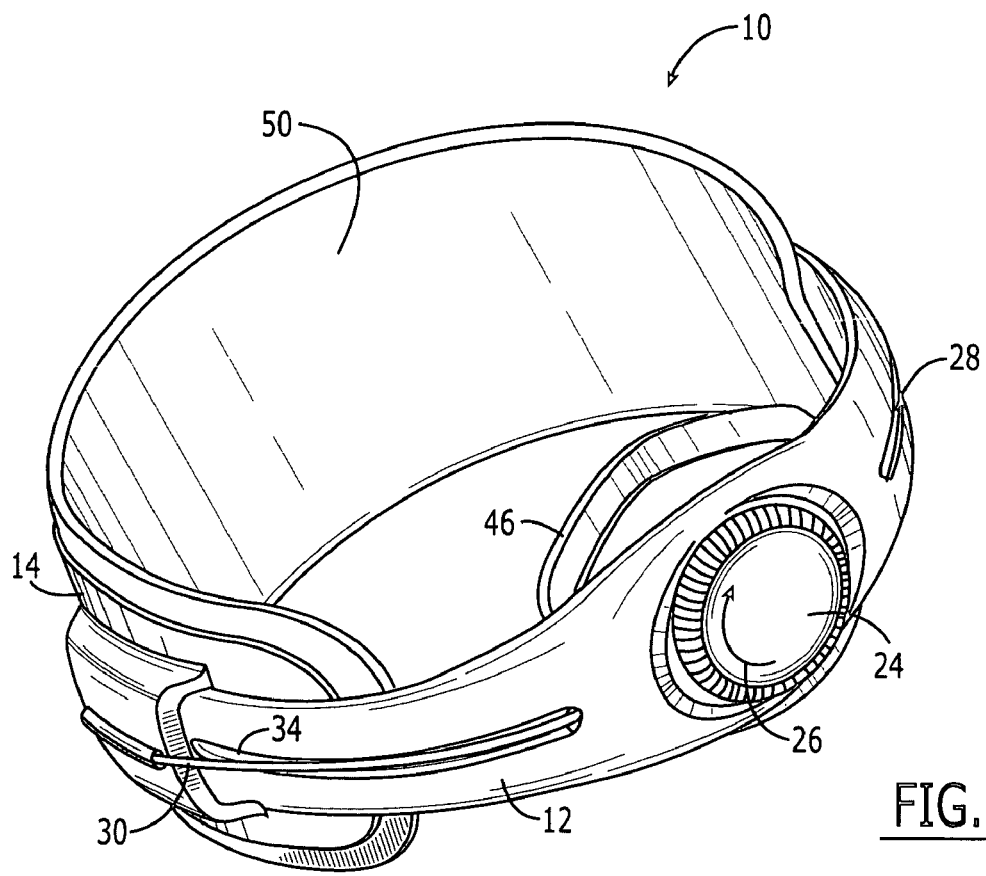
FIG. 1 is a perspective view of a first embodiment of the invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein-as understood by the Ordinary Artisan based on the contextual use of such term-differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers. " Finally, when used herein to join a list of items, "and" denotes "all of the items of the list." Thus, reference to "a picnic basket having cheese and crackers" describes "a picnic basket having cheese, wherein the picnic basket further has crackers, " as well as describes "a picnic basket having crackers, wherein the picnic basket further has cheese."

Figure 5:
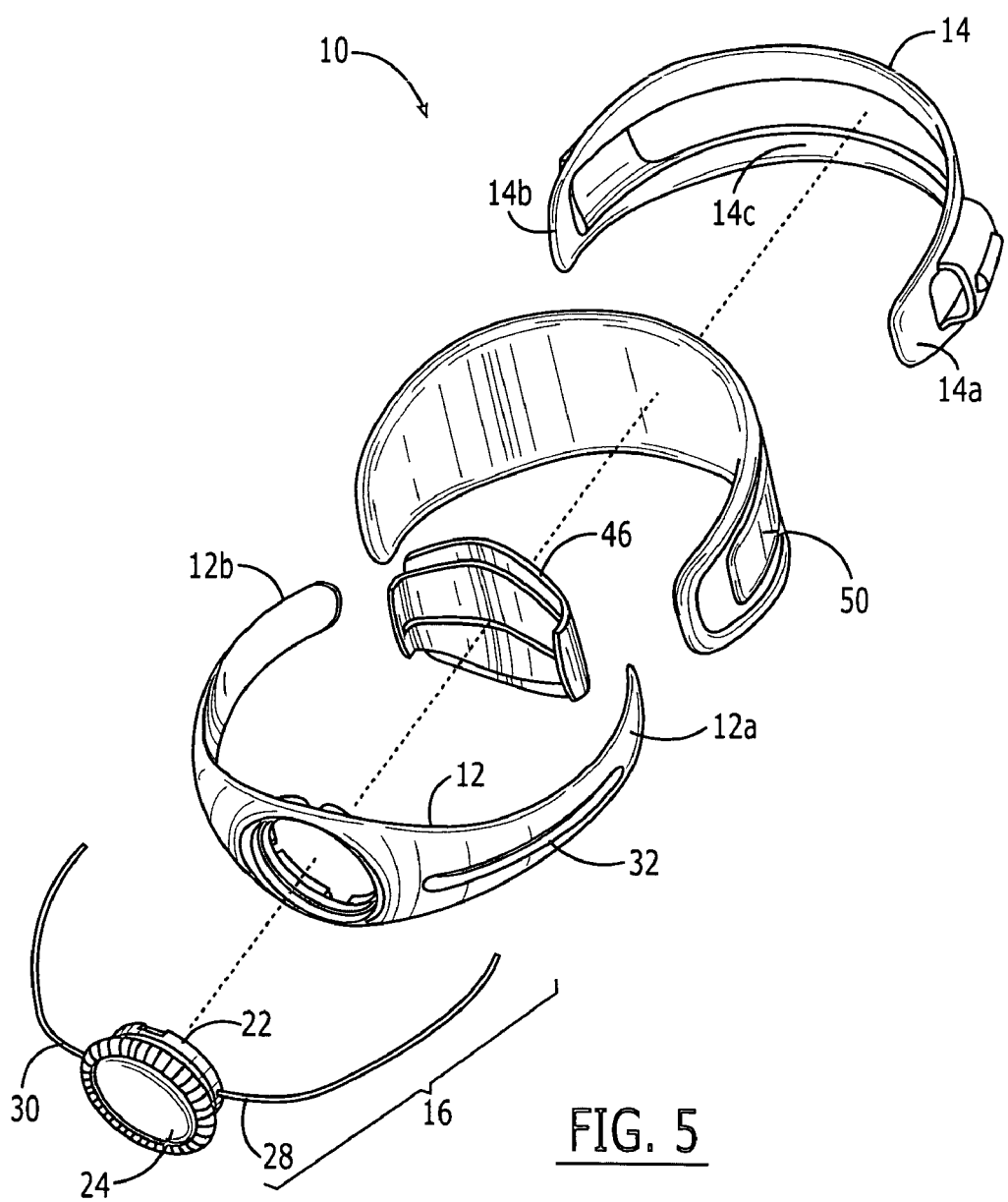
FIG. 5 is an exploded perspective view of the embodiment of FIG. 1.
Figure 6:
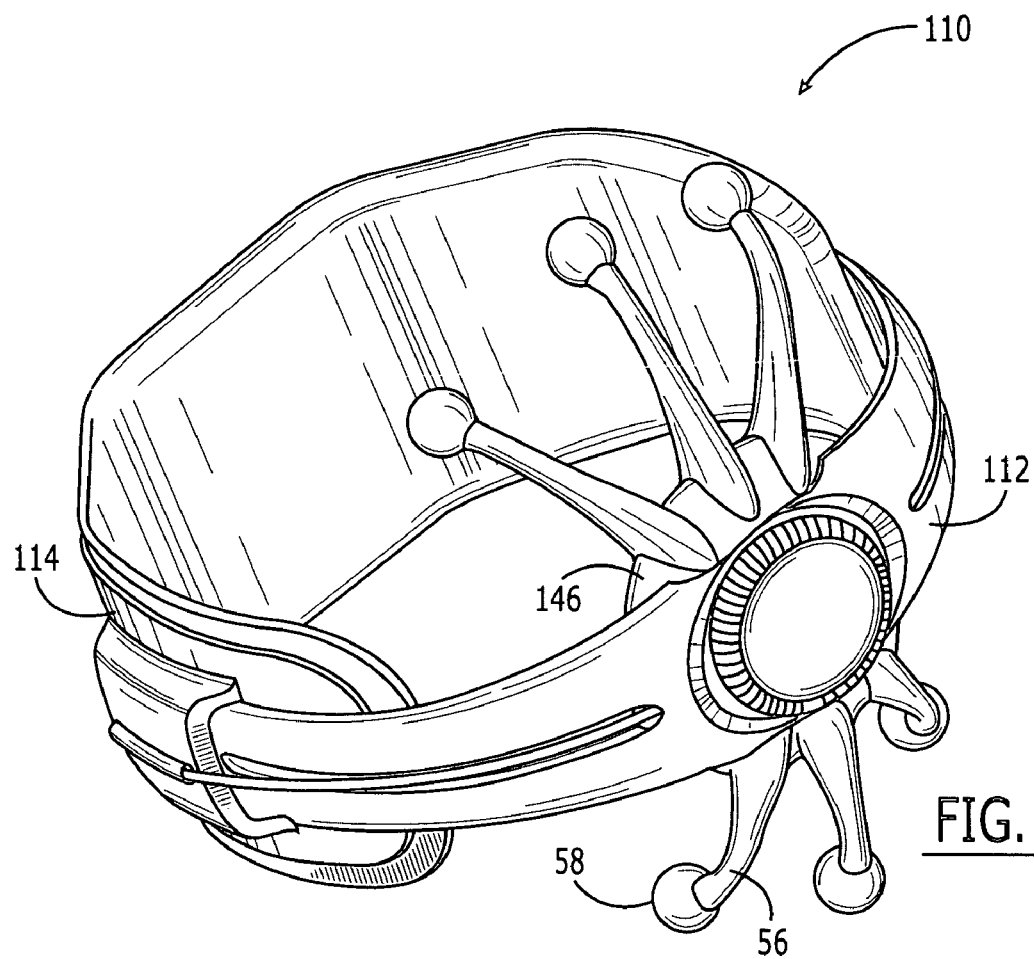
FIG. 6 is a perspective view of a second embodiment of the invention.
Figure 7:
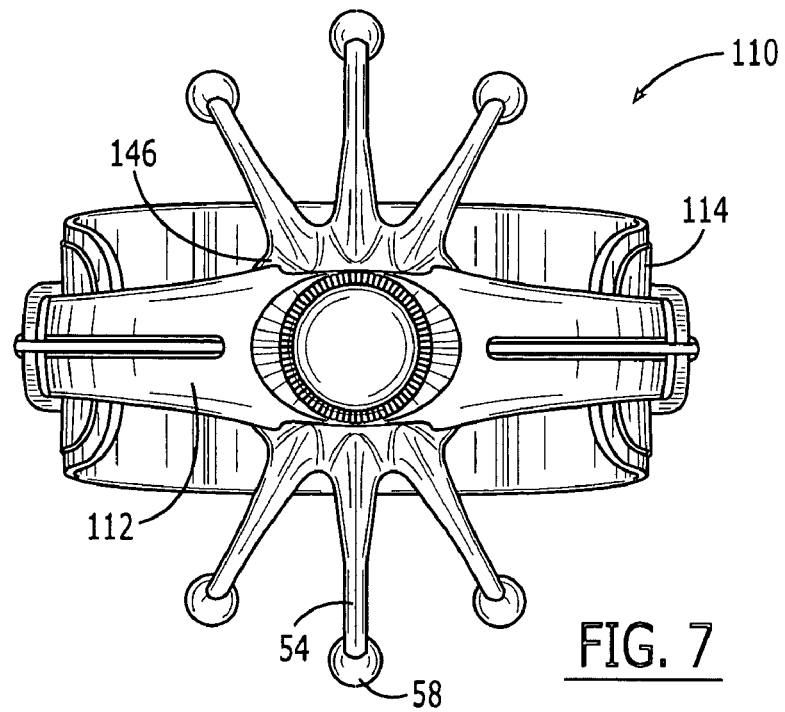
FIG. 7 is front elevational view of the embodiment of FIG. 6.

Turning now to the figures, a first embodiment of the invention is shown in FIGS. 1-5. An apparatus 10 for circumferential disposition on an appendage such as an arm or leg comprises a first partial collar 12, a second partial collar 14, and a tensioning system 16 (FIG. 5). The first partial collar 12 and second partial collar 14 are each adapted for partially encircling an appendage such that together they completely encircle an appendage when the apparatus 10 is disposed on the appendage. Though other embodiments of the invention are adapted for disposition on other areas of other appendages, the first embodiment of the invention, namely the apparatus 10, is particularly adapted for disposition on an arm. For example, in FIG. 11 the apparatus 10 is disposed on an arm beyond the elbow. In this disposition, the apparatus 10 is nominally referred to as an elbow brace.

Figure 11:
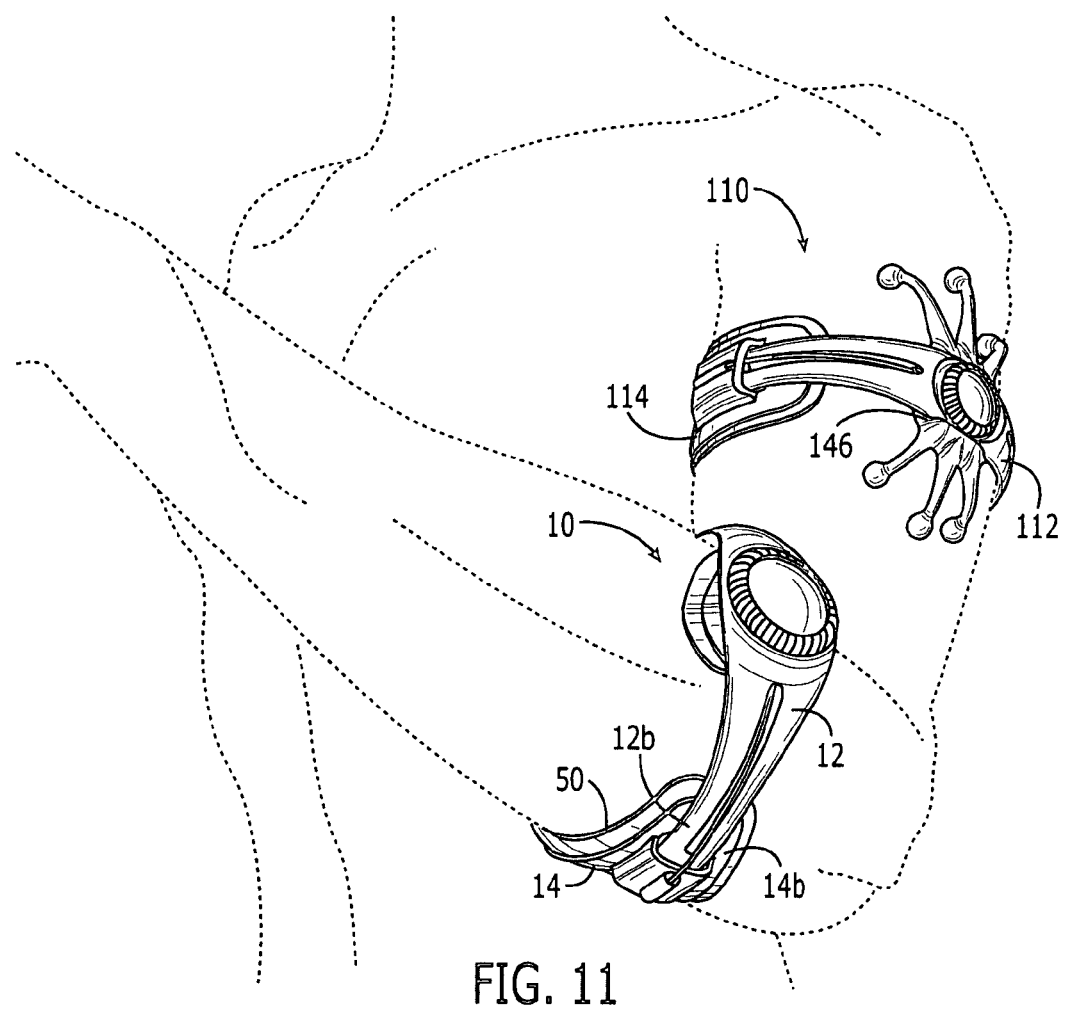
FIG. 11 is an environmental perspective view showing the embodiment of FIG. 1 disposed as an elbow brace on an arm, and the embodiment of FIG. 6 disposed as a shoulder brace on the arm.

The tensioning system 16 (FIG. 5) draws together the first partial collar 12 and second partial collar 14. When the apparatus 10 is disposed on an appendage as shown in FIG. 11, the first partial collar 12 and second partial collar 14 are drawn together by the tensioning system (FIG. 5) and respective forces are thereby applied to the appendage by the partial collars. In particular, the first partial collar 12 is capable of applying a first force 18 (FIG. 3) to a first side of and appendage and the second partial collar 14 is capable of applying a second force 20 to a second side of the appendage, wherein the first force 18 and second force 20, when applied, generally oppose one another.

The partial collars 12 and 14 are each generally rigid, or at least semirigid. Exemplary materials for their construction include, but are not limited to: plastics, particularly moldable and injection-moldable plastics; Nylon 66; fiberglass; carbon and carbon composites; polycarbonate; polyoxymethylene; polymethylmethacrylate (PMMA); polyacetal; urea-formaldehyde; polystyrene; and vinyl polymers.

Together, particularly when drawn together by the tensioning system 16, the partial collars 12, 14 define a collar clamp that closes upon an appendage and applies the directionally opposing forces 18, 20. Thus, opposing forces are applied to opposing sides of an appendage and can be so applied, if desired, without any substantial circumferential forces being applied about the appendage as a function of the rigidity of the partial collars and/or use of pressure applicators. Whereas circumferential forces such as those of a tourniquet tend to interfere with blood circulation, the opposing forces 18, 20 applied by the apparatus 10 allow blood flow through an appendage encircled by the apparatus while still effecting side-to-side tissue compression of the appendage. Thus, the inventive coapting apparatus 10 provides, among other things, benefits that include: deflection of muscle forces; functional shortening of muscle length; and the maintenance of neurovascular channels.

The tensioning system 16 (FIG. 5) comprises a device 22 for controllably varying the forces applied to an appendage encircled by the apparatus 10. In particular, a rotatable control knob 24 depends from the device 22 for grasping and rotation thereof by a wearer or user of the apparatus 10. Upon rotation of the rotatable control knob 24 in a first rotational direction 26 (FIGS. 1-2), the directionally opposing forces 18, 20 (FIG. 3) applied to an appendage encircled by the apparatus 10 are increased. In particular, the forces are increased by the drawing together of the first and second partial collars 12, 14 upon rotation of the rotatable control knob 24 in the first rotational direction 26. It should be understood that, while the first rotational direction 26 is illustrated as clockwise in FIGS. 1-2, the descriptions herein similarly may relate to counter-clockwise rotations as well.

Furthermore, by pressing of the rotatable control knob 24, the directionally opposing forces 18, 20 applied to an appendage are decreased or are entirely terminated. Thus, in the first embodiment of the invention, the apparatus 10 closes upon rotation of the rotatable control knob and tends to spring back open upon pressing of the control knob. The apparatus 10 closes in that the second partial collar 14 moves relative to the first partial collar 12 in a first direction 31, thereby, increasing the forces 18, 20 (FIG. 3) when the apparatus is clamped in engagement with an appendage. The apparatus opens in that the second partial collar 14 moves relative to the first partial collar 12 in a second direction 32, thereby decreasing the forces 18, 20 when the apparatus is tightly clamped in engagement with an appendage.

In another embodiment of the invention, not illustrated, a coapting shell encircling an appendage closes upon rotation of a rotatable control knob in one rotational direction and opens upon rotation of the rotatable control knob in an opposite rotational direction.

In yet another embodiment of the invention, not illustrated, a coapting brace for encircling an appendage and applying forces thereto applies increasing forces upon rotation of a control knob and releases the forces upon pulling of the knob outwardly from the brace. It should be apparent that the present invention has many embodiments and the descriptions herein of particular tensioning systems and control devices are provided as examples and are not to be construed as limitations of the invention.

Nonetheless, in order to provide detailed descriptions of one or more particular embodiments, the tensioning system 16, as shown in the exploded view of FIG. 5, comprises the rotary device 22, a first line portion 28 depending from the rotary device, and a second line portion 30 depending from the rotary device. Upon rotation of the rotatable control knob 24 in the first rotational direction 26 (FIG. 1), the tensioning lines are retracted and the line portions 28, 30 are retracted and shorten. The first and second partial collars are thereby drawn together, thereby closing the apparatus 10 (FIG. 3) and increasing forces applied to an appendage. Upon pressing of the rotatable control knob 24, the tensioning lines are mechanically released and the line portions 28, 30 tend to lengthen. The apparatus 10 (FIG. 3) is thereby opened and forces applied to an appendage are thereby decreased.

An exemplary releasable and adjustable rotary device comprises a housing within which are incrementally drawn multiple lines upon selective rotation of a control knob. Such an exemplary rotary device is disclosed, for example, in U.S. Pat. No. 5,042,177 to Schoch, titled "Rotary Closure for a Sports Shoe, Especially a Ski Shoe," which patent is hereby incorporated herein by reference.

Figure 2:
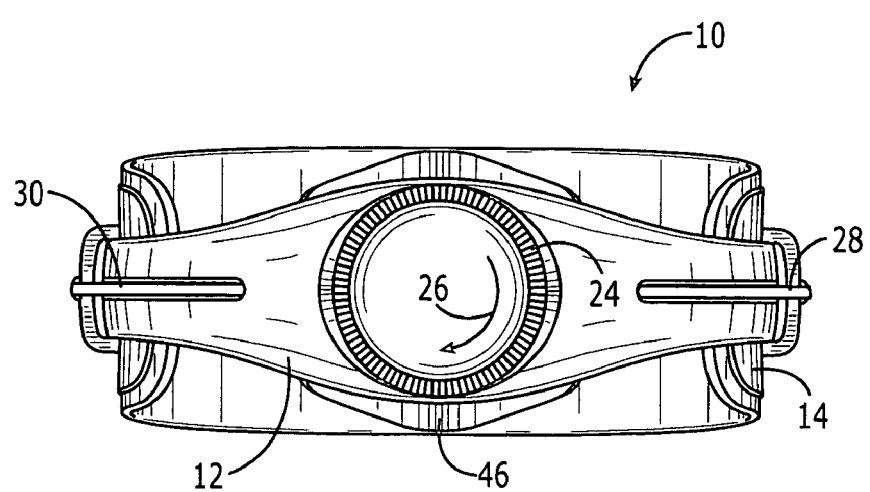
FIG. 2 is front elevational view of the embodiment of FIG. 1.

As shown in FIGS. 1, 2, and 5, the first line portion and second line portion depend from the rotary device 22 and extend, in opposite directions, partially circumferentially about the first partial collar 12. Guide channels 32 (FIG. 5) and 34 (FIG. 1) are defined by the first partial collar 12 for receiving and guiding respective line portions 28, 30 and maintaining the courses of the lines within margins of the apparatus. Each line portion 28, 30 is furthermore attached at a terminus thereof to the second partial collar. As the line portions 28, 30 are drawn partially into the housing of the rotary device 22 upon rotation of the rotatable control knob 24, the first and second partial collars are thereby drawn together.

In another embodiment of the invention (not illustrated), first and second line portions that depend from a rotary device are opposing ends of a single line. The rotary device and single line completely encircle an apparatus that comprises two coapting partial collars. When the apparatus is circumferentially disposed on an appendage, the rotary device and continuous line completely encircle the appendage.

In the first embodiment of the invention each line portion 28, 30 comprises a flexible and inextensible line. The line portions 28, 30 are illustrated in FIGS. 1-5 as monofilament lines though these descriptions relate as well to multifilament lines and many types of elongate flexible lines having various constructions and formed of various materials having respective tensile and flexible properties. Exemplary constructions include, but are not limited to: monofilament lines, multifilament lines, wound lines, woven lines, braided lines, layered lines, strings, ropes, cords, threads, twines, intertwined strands, chains, tethers, belts, bands, straps, and combinations thereof. Exemplary materials include, but are not limited to: natural fibers including hemp, cotton, linen, hide, gut, and sinew; synthetic and plastic fibers such as nylon, polyethylene, and fluorocarbon; lines formed of metals such as wires and cables, in particular wound steel cables; and, combinations thereof.

Figure 3:
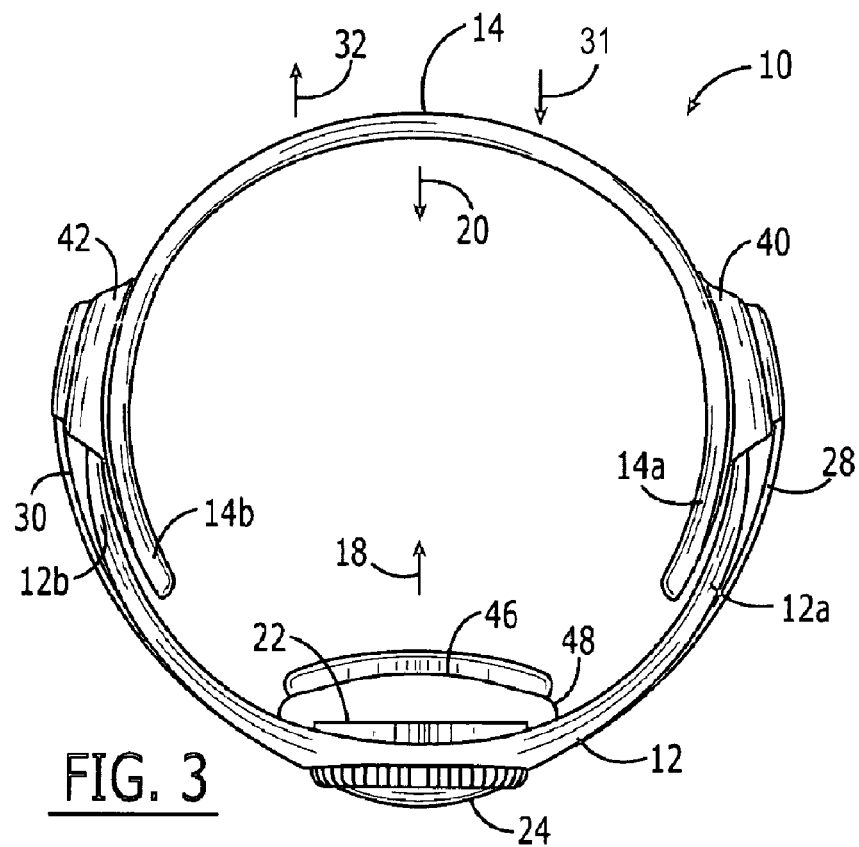
FIG. 3 is a plan view of the embodiment of FIG. 1.
Figure 4:
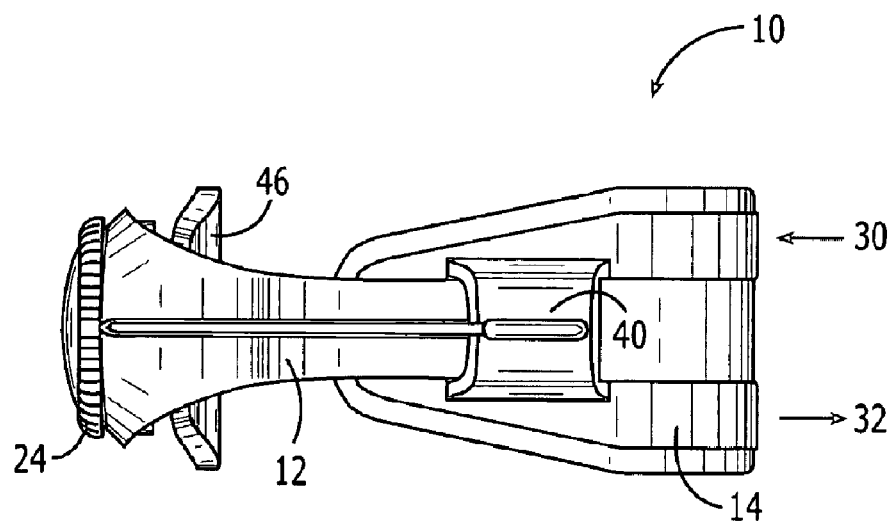
FIG. 4 is side elevational view of the embodiment of FIG. 1.

As shown in FIG. 5, each partial collar 12, 14 comprises an open, arcuate C-shape. The first partial collar 12 comprises opposing end portions 12a, 12b. Similarly, the second partial collar 14 comprises opposing end portions 14a, 14b. When the apparatus is assembled as shown in FIG. 3, opposing end portions 14a, 14b of the second partial collar are disposed in the interior of the open C-shape of the first partial collar 12. Consequentially, when the apparatus 10 is circumferentially disposed on an appendage, the opposing end portions 14a, 14b of the second partial collar 14 are disposed between the appendage and respective opposing end portions 12a, 12b of the first partial collar 12. For example, as shown in FIG. 11, when the apparatus 10 is circumferentially disposed on an appendage, the end portion 14b of the second partial collar 14 is disposed between the appendage and the end portion 12b of the first partial collar 12.

As shown in FIG. 3, the second partial collar 14 comprises a pair of channels or conduits 40, 42 for receiving respective end portions 12a, 12b of the first partial collar 12. The conduits 40, 42 assist in maintaining a coapting engagement of the first partial collar 12 and second partial collar 14. The conduits 40, 42 furthermore maintain the relative orientations of the partial collars. The opposing end portions 12a, 12b pass freely within the respective conduits 40, 42 allowing relative movement of the partial collars in closing and opening of the apparatus 10. For example, the end portion 12a of the first partial collar passes freely into the conduit 40 as the apparatus 10 closes by movement of the second partial collar 14 relative to the first partial collar 12 in the first direction 31.

As further shown in FIG. 3, the apparatus 10 comprises a pressure applicator 46 attached to the first partial collar 12. When the apparatus is circumferentially disposed about an appendage, the pressure applicator 46 applies pressure to a discrete area of the appendage according to the disposition of the apparatus. The pressure applicator, optionally somewhat flexible to allow mild deflection of the applicator while applying pressure to an appendage, is constructed of a material capable of bearing a load and optionally allowing mild deflection. Exemplary materials include, but are not limited to: plastic; fiberglass; carbon and carbon composites; and spring steel. In the first embodiment of the invention, the pressure applicator 46 comprises a leaf spring 48 attached to the first partial collar. The pressure applicator 46 is optionally padded to provide for comfort as it applies pressure to a discrete area of an appendage. The pressure applicator 46 is optionally removable from the apparatus 10.

The first and second partial collars are each optionally padded for comfort of the wearer of the apparatus 10. For example, a collar pad 50 (FIG. 5) is adapted to nestle within the second partial collar 14 as shown in FIG. 1 for disposition between the second partial collar 14 and an appendage when the apparatus 10 is disposed on the appendage as shown in FIG. 11. The collar pad 50 preferably comprises soft, breathable, and washable materials. Exemplary materials include, but are not limited to, natural and synthetic fabrics, pliable foams, elastic fabrics, neoprene, spandex, felt, natural and synthetic chamois, and various stretchable and pliable materials.

In the first embodiment of the invention, each partial collar defines a respective arcuate receiving area. For example, the second partial collar 14 of the apparatus 10 defines an arcuate, cylindrically-concave receiving area 14c (FIG. 5) for receiving a side of an appendage. The apparatus 10 is particularly illustrated for use as an elbow brace in FIG. 11. The arcuate receiving area of the second partial collar comfortably receives, for example, the volar side of a forearm proximal an elbow as shown in FIG. 11.

Figure 10:
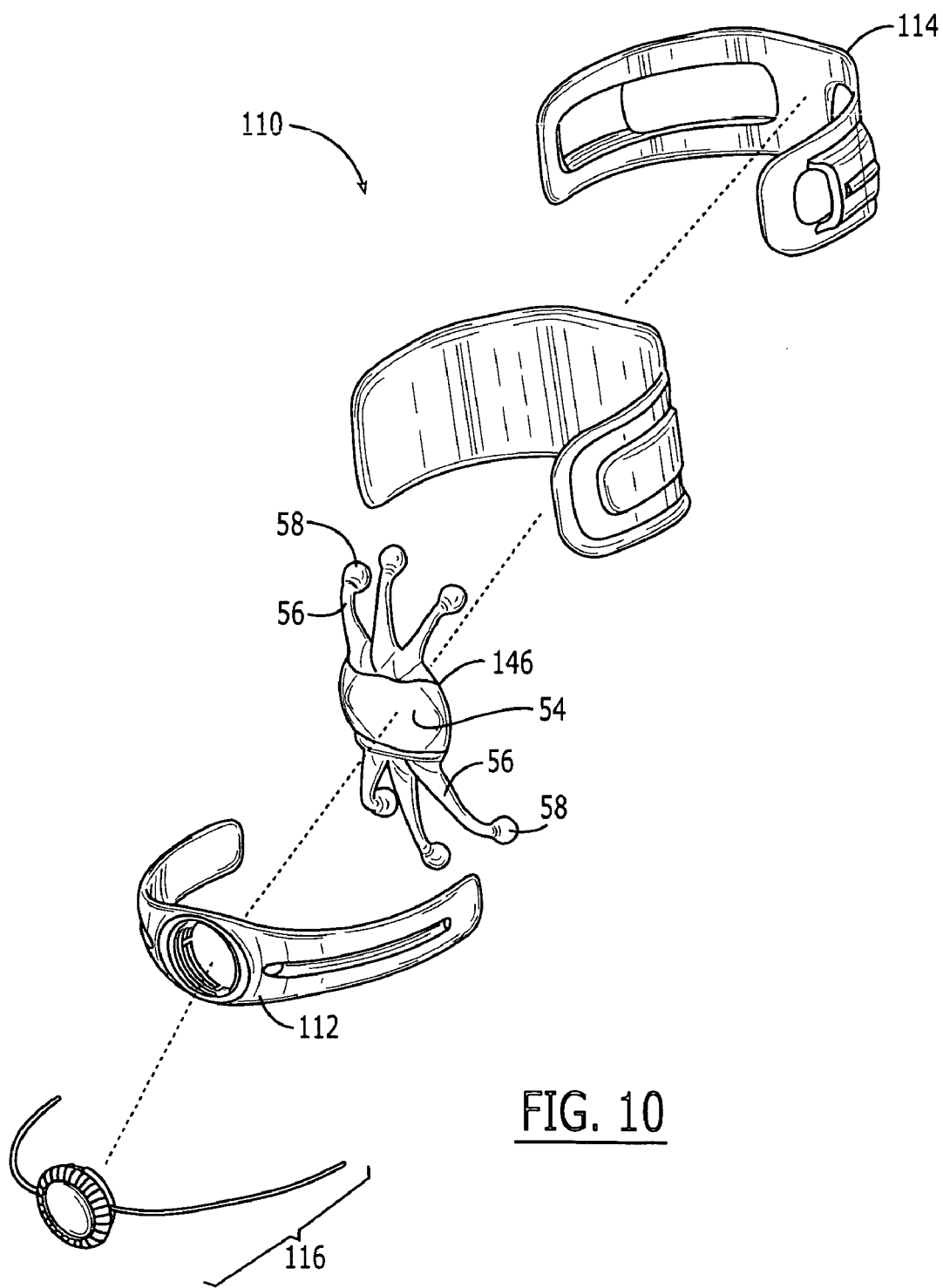
FIG. 10 is an exploded perspective view of the embodiment of FIG. 6.

Turning now to a second embodiment shown in various views in FIGS. 6-10, an apparatus 110 for circumferential disposition on an appendage such as an arm or leg comprises a first partial collar 112, a second partial collar 114, and a tensioning system 116 (FIG. 10). The first partial collar 112 and second partial collar 114 are each adapted for partially encircling an appendage such that together they completely encircle an appendage when the apparatus 110 is disposed on the appendage. For example, in FIG. 11 the apparatus 110 is disposed on an arm proximal a shoulder. In this disposition, the apparatus 110 is nominally referred to as a shoulder brace.

The tensioning system 116 (FIG. 10) draws together the first partial collar 112 and second partial collar 114. When the apparatus 110 is disposed on an appendage as shown in FIG. 11, the first partial collar 112 and second partial collar 114 are drawn together by the tensioning system 116 (FIG. 10). Respective forces are thereby applied to the appendage by the partial collars. In particular, the first partial collar 112 is capable of applying a first force 118 (FIG. 8) to a first side of an appendage and the second partial collar 114 is capable of applying a second force 120 to a second side of the appendage. As the second side of the appendage is opposite the first side of the appendage, the first force 118 and second force 120, when applied, generally oppose each other.

Figure 8:
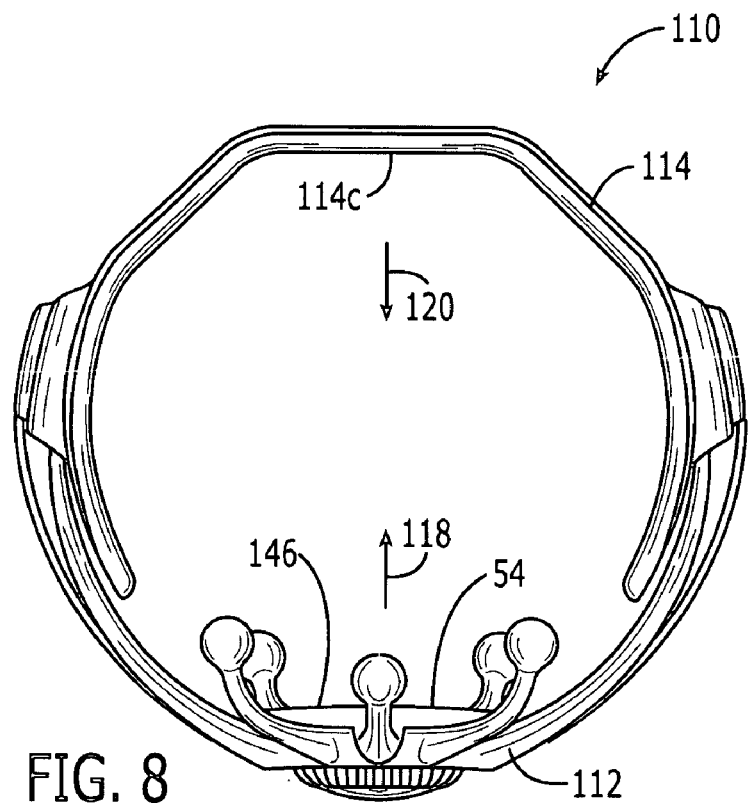
FIG. 8 is a plan view of the embodiment of FIG. 6.
Figure 9:
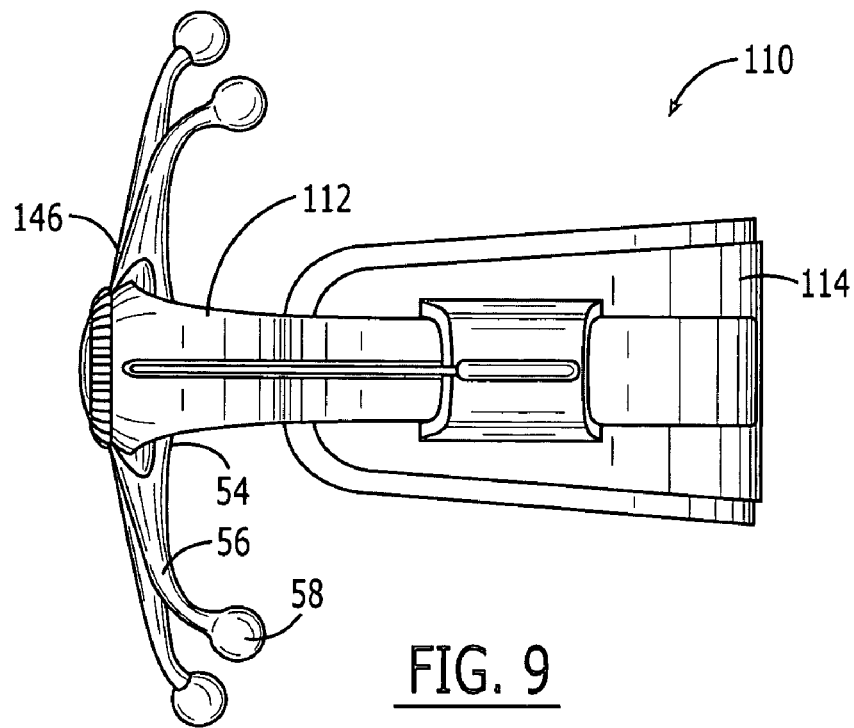
FIG. 9 is side elevational view of the embodiment of FIG. 6.

The partial collars 112 and 114 are each generally rigid, or at least semirigid. Together, particularly when drawn together by the tensioning system 116 (FIG. 10), the partial collars 112 and 114 define a collar clamp that closes upon an appendage and applies the directionally opposing forces 118, 120 (FIG. 8). Thus, opposing forces are applied to opposing sides of an appendage and can be so applied, if desired, without any considerable circumferential forces being applied about the appendage as a function of the rigidity of the partial collars and/or use of pressure applicators. Generally applying only opposing forces 118, 120 by the apparatus 110 allows blood flow through the appendage even though it is surrounded by the apparatus and even though side-to-side tissue compression is applied to the appendage. Thus the inventive apparatus 110 provides, among other things, benefits that include: deflection of muscle forces; functional shortening of muscle length; and the maintenance of neurovascular channels.

The apparatus 110 of FIGS. 6-10 bears many similarities to the apparatus 10 of FIG. 1-5. Therefore, many of the descriptions herein relate to both apparatus 10 and apparatus 110. However, in the interest of providing descriptions of the present invention that has many embodiments, and in the interest of minimizing duplicative descriptions, the descriptions below relate particularly to features and benefits of the apparatus 110 that are generally not merely duplicative to those of the apparatus 10.

For example, as shown in FIG. 8, the second partial collar 114 defines a polygonal concave receiving area 114c for receiving a side of an appendage. The apparatus 110 is particularly illustrated for use as a shoulder brace in FIG. 11. The polygonal concave receiving area 114c (FIG. 8) of the second partial collar 114 comfortably receives, for example, the volar side of an upper arm just below the shoulder. An arterial pressure point resides proximal this area of the arm. The rigid partial collar 114, having planar facets defining the polygonal concave receiving area 114c, is capable of applying the force 120 (FIG. 8) while minimizing the restriction of blood flow in the arm, and is furthermore capable of allowing comfortable swinging movement of the arm relative to the nearby rib-cage of the torso.

For further example, while the pressure applicator 46 of FIGS. 1-5 does not generally extend significantly beyond margins of the partial collar 12, other embodiments of pressure applicators contact areas of appendages beyond margins of the partial collars. For example, an outrigger 146 for contacting multiple areas of an appendage is shown in FIGS. 6-10. When attached to the first partial collar 112 as illustrated in FIGS. 6-9, the outrigger 146 contacts and applies pressure to multiple areas of an appendage (FIG. 11) on which the apparatus 110 is circumferentially disposed. As shown in FIG. 10, the outrigger 146 comprises a base 54, multiple members 56 attached to the base, and pressure applicators 58 respectively attached to the members 56.

The outrigger 146 optionally comprises a rigid unitary construction formed, for example, of hard plastic. Alternatively, the members 56 of the outrigger 146 are optionally spring loaded or are articulated by cables. The members 56 may be rigid and fixed, or may be formable. The members may be positionable like jointed fingers. Furthermore, the members may be removable from the base 54 such that they may be replaced or such that a variable number of members depends from the base.

With regard to each of the pressure applicators described herein, for example pressure applicator 46 of FIGS. 1-5 and pressure applicators 146 of FIGS. 6-10, a pressure applicator according to the present invention optionally comprises an active cell (not illustrated). An "active cell" as used herein relates to an electrical, mechanical, or electromechanical device that, in conjunction with pressure applied by a pressure applicator, applies stimulus or treatment. For example, one embodiment of an active cell applies vibratory waves for massaging or otherwise stimulating tissue and vessels. In another example, an active cell applies acoustic waves. In another example, an active cell applies electrical stimulation or conveys electrical current. In yet another example, an active cell applies heating, cooling, or thermal-cycling therapy.

What is claimed is:

1. A method for applying pressure to a person's body, comprising the steps of:
   (a) positioning first and second components on opposite sides of a person's arm;
   (b) drawing together a first end of the first component and a first end of the second component; and
   (c) drawing together a second end of the first component and a second end of the second component;
   (d) wherein one of the components includes a rotary device and tensioning lines that extend from the rotary device to the other component, the rotary device and tensioning lines being used for drawing together the components to thereby apply pressure to opposite sides of the arm
   (e) wherein the components are at least semirigid and have limited pressuring engagement with the arm when the first and second components are drawn together, the first and second components engaging and applying substantial pressure to the arm proximate respective middle portions of the first and second components but not proximate the ends of the first and second components.

2. The method of claim 1, further comprising the step of securing said drawn components together in their pressure-applying disposition about the arm.

3. The method of claim 1, wherein the rotary device includes a control knob, and wherein rotation of the control knob in a first rotational direction retracts the tensioning lines for increasing the pressure applied by the first and second components to the arm.

4. The method of claim 3, wherein pressing of the control knob releases the tensioning lines for decreasing of the pressure applied to the arm by the first and second components.

5. The method of claim 1, wherein the rotary device and tensioning lines are used for drawing together the first ends of the first and second components in said step (b).

6. The method of claim 1, wherein the rotary device and tensioning lines are used for drawing together the second ends of the first and second components in said step (c).

7. The method of claim 1, wherein the rotary device and tensioning lines are used for drawing together the first ends and the second ends of the first and second components in said steps (b) and (c).

8. The method of claim 1, wherein the first component is generally C-shaped and the second component is generally C-shaped.

9. An apparatus for applying pressure to a person's body, comprising:
   (a) a first partial collar configured to partially surround a first side of an appendage of a person;
   (b) a second partial collar configured to partially surround a second, opposite side of the appendage; and
   (c) a tensioning system joining together said first partial collar and said second partial collar, said tensioning system being operable to draw together said first partial collar and said second partial collar to compress the appendage between said first partial collar and said second partial collar, said tensioning system including a rotary closure device operable to selectively draw said first partial collar and said second partial collar together;
   (d) wherein said first and second partial collars collectively define a collar that is configured to attach to the appendage such that the appendage axially extends beyond opposite axial ends of the collar; and
   (e) wherein the first partial collar and the second partial collar are at least semirigid and have limited pressuring engagement with the person's body when the first and second partial collars are drawn together, the first and second partial collars engaging and applying substantial pressure to the person's body proximate respective middle portions of the first and second partial collars but not proximate opposed ends of the first and second partial collars.

10. An apparatus for applying pressure to a person's body, comprising:
    (a) a first component for receiving one side of an appendage of a person;
    (b) a second component for receiving the other side of the appendage; and
    (c) a tensioning system configured to join said first component to said second component in a disposition about the appendage such that said first component applies a first force to the appendage and said second component applies a second force to the appendage, the first force being generally opposed to the second force, said tensioning system including a rotary closure device located on said first component and at least one tensioning line extending from said rotary closure device and being affixed to said second component, said rotary closure device being operable to selectively draw said first component and said second component together;
    (d) wherein the first component and the second component are at least semirigid and have limited pressuring engagement with the person's body when the first and second components are drawn together, the first and second components engaging and applying, through the opposed first and second forces, substantial pressure to the person's body proximate respective middle portions of the first and second components but not proximate opposed ends of the first and second components, whereby side-to-side tissue compression can be achieved without tourniquet-like circumferential forces being applied by the first and second components.

11. A method for applying pressure to a person's body, comprising:
    (a) positioning a first component to partially surround a first side of a portion of the person's body;
    (b) positioning a second component to partially surround a second, opposite side of the portion of the person's body; and
    (c) drawing together the first component and the second component to compress the portion of the person's body between the first component and the second component using a tensioning system that joins the first component and the second component;
    (d) wherein the tensioning system comprises a rotary device located on the first component and at least one tensioning line that extends from the rotary device and is affixed to the second component; and
    (e) wherein the first component and the second component are at least semirigid and have limited pressuring engagement with the person's body when the first and second components are drawn together, the first and second components engaging and applying substantial pressure to the person's body proximate respective middle portions of the first and second components but not proximate opposed ends of the first and second components, whereby side-to-side tissue compression can be achieved without tourniquet-like circumferential forces being applied by the first and second components.

12. A method for applying pressure to a person's body, comprising:
(a) positioning a first component to partially surround a first side of a portion of a person's body;
(b) positioning a second component to partially surround a second, opposite side of he portion of the person's body; and
(c) drawing together the first component and the second component to compress the person's body between the first component and the second component using a tensioning system that joins the first component and the second component; and
(d) selectively applying pressure to the appendage using an outrigger that is attached to the first component, the outrigger including a base having a plurality of removable members attached thereto and pressure applicators respectively attached to the members and extending beyond opposite sides of the first component that engage areas of the person's body not covered by the first component.

13. An apparatus for applying pressure to a person's body, comprising:
(a) a first component for receiving one side of an appendage;
(b) a second component for receiving the other side of the appendage; and
(c) a tensioning system configured to join said first component to said second component in a disposition about the appendage such that said first component applies a first force to the appendage and said second component applies a second force to the appendage, the first force being generally opposed to the second force;
(d) wherein said tensioning system comprises a rotary device attached to said first component;
(e) wherein said first component and said second component collectively define a collar that is configured to attach to and completely encircle an appendage of the person's body such that the appendage axially extends beyond opposite axial ends of the collar; and
(f) wherein said rotary device is attached to said first component;
(g) wherein said rotary device includes a rotatable control knob, a first line portion depending from said rotary device and affixed to said second component, and a second line portion depending from said rotary device and affixed to said second component; and
(h) wherein rotation of said rotatable control knob in a first rotational direction causes shortening of at least one of said first line portion and said second line portion thereby drawing together said first component and said second component.

14. The apparatus of claim 13, wherein said first line portion extends at least partially about said first component in a first circumferential direction, and said second line portion extends at least partially about said first component in a second, circumferential direction opposite to the first circumferential direction.

15. An apparatus for applying pressure to a person's body, comprising:
(a) a first component for receiving one side of an appendage of a person's body;
(b) a second component for receiving the other side of the appendage;
(c) a tensioning system configured to join said first component to said second component in a disposition about the appendage such that said first component applies a first force to the appendage and said second component applies a second force to the appendage, the first force being generally opposed to the second force; and
(d) an outrigger attached to said first component, said outrigger including a base having a plurality of removable members attached thereto and pressure applicators respectively attached to the members and extending beyond opposite sides of said first component for applying pressure to the appendage at areas thereof not covered by said first component.

16. A method for applying pressure to a person's body, comprising:
(a) positioning a first component to partially surround a first side of a person's body;
(b) positioning a second component to partially surround a second, opposite side of the person's body; and
(c) drawing together the first component and the second component to compress the person's body between the first component and the second component using a tensioning system that joins the first component and the second component;
(d) wherein the first component comprises opposing end portions and the second component comprises opposing end portions, the opposing end portions of the first component overlapping an exterior side of the opposing end portions of the second component such that the opposing end portions of the second component are located between the opposing end portions of the first component and the person's body;
(e) wherein the opposing end portions of the second component each comprises a channel on the exterior side thereof within which a respective one of the opposing end portions of the first component extends during the drawing together of the first component and the second component for compressing the person's body; and
(f) wherein the first component and the second component are sufficiently rigid such that drawing of the first and second components together applies opposing forces to the person's body proximate respective middle portions of the first and second components, whereby side-to-side tissue compression can be achieved without tourniquet-like circumferential forces being applied.

17. An apparatus for applying pressure to a person's body, comprising:
(a) a first component for receiving one side of a portion of a person's body;
(b) a second component for receiving the other side of the portion of the person's body; and
(c) a tensioning system configured to join said first component to said second component in a disposition about the portion of the person's body such that said first component applies a first force to the portion of the person's body and said second component applies a second force to the portion of the person's body, the first force being generally opposed to the second force;
(d) wherein said first component comprises opposing end portions and said second component comprises opposing end portions, said opposing end portions of said first component overlapping an exterior side of said opposing end portions of said second component such that said opposing end portions of said second component are located between said opposing end portions of said first component and the portion of the person's body;
(e) wherein said opposing end portions of said second component each comprises a channel on said exterior side thereof within which a respective one of said opposing end portions of said first component is extends during the drawing together of the first component and the second component for compressing the person's body; and (f) wherein said first component and said second component are sufficiently rigid such that drawing of said first and second components together applies opposing forces to the person's body proximate respective middle portions of said first and second components, whereby side-to-side tissue compression can be achieved without tourniquet-like circumferential forces being applied.

18. A method for applying pressure to a person's body comprising:
    (a) positioning a first component configured to partially surround a first side of a person's body;
    (b) positioning a second component configured to partially surround a second, opposite side of the person's body; and
    (c) drawing together the first component and the second component while applying pressure to a portion of the person's body using a pressure applicator that is attached to the first component and that engages the portion of person's body, the pressure applicator including a leaf spring.

19. The method of claim 18, wherein the pressure applicator extends beyond a side of the first component for applying pressure to the portion of the person's body at an area thereof that is not covered by the first component.

20. An apparatus for applying pressure to a person's body, comprising:
    (a) a first component for receiving one side of an appendage;
    (b) a second component for receiving the other side of the appendage;
    (c) a tensioning system configured to join said first component to said second component in a disposition about the appendage such that said first component applies a first force to the appendage and said second component applies a second force to the appendage, the first force being generally opposed to the second force; and
    (d) a pressure applicator attached to said first component for engaging an area of the appendage, said pressure applicator including a leaf spring.

21. The apparatus of claim 20, wherein said pressure applicator extends beyond a side of said first component for applying pressure to the appendage at an area thereof that is not covered by said first component.

22. A method for applying pressure to a person's body, comprising the steps of:
    (a) positioning first and second partial collars such that the first partial collar surrounds at least a first side of a person's body and the second partial collar surrounds at least a second, opposite side of the person's body, and such that the first and second partial collars collectively define a collar that attaches to the appendage such that the appendage axially extends into and out of the collar on opposite axial ends of the collar; and
    (b) drawing together the first partial collar and the second partial collar using a tensioning system such that a portion of the person's body is compressed between the first partial collar and the second partial collar;
    (c) wherein the tensioning system includes a rotary closure device operable to selectively draw the first partial collar and the second partial collar together; and
    (d) wherein the first and second partial collars are at least semirigid and have limited pressuring engagement with the person's body when the first and second partial collars are drawn together, the first and second partial collars engaging and applying substantial pressure to the person's body proximate respective middle portions of the first and second partial collars but not proximate opposing ends of the first and second partial collars.

23. The method of claim 22, wherein the tensioning system includes a releasable and adjustable rotary device comprising a housing within which is incrementally drawn a portion of a tensioning line upon selective rotation of the control knob such that the first partial collar and the second partial collar are drawn together.

24. The method of claim 23, further comprising mechanically releasing the tensioning line such that a portion of the tensioning line may be withdrawn from the housing.

25. The method of claim 22, wherein said step (a) comprises positioning the first and second partial collars on opposite sides of a person's arm.

26. The method of claim 25, wherein performance of said step (b) effects side-to-side tissue compression of the arm but does not result in circumferential forces being applied about the arm so as to interfere with blood circulation through the arm.

27. The method of claim 26, wherein the first and second partial collars are positioned on opposite sides of a person's arm proximal the elbow.

28. The method of claim 26, wherein the first and second partial collars are positioned on opposite sides of a person's arm proximal the shoulder.

29. The method of claim 22, wherein said step (a) comprises positioning the first and second partial collars on opposite sides of a person's leg.

30. The method of claim 22, wherein the first partial collar and the second partial collar collectively define a collar that completely encircles the appendage extending therethrough.

31. A method for applying pressure to a person's body, comprising the steps of:
    (a) positioning first and second components such that the first component surrounds at least a first side of a person's body without spanning a joint of the person's body and the second component surrounds at least a second, opposite side of the person's body without spanning a joint of the person's body; and
    (b) drawing together the first component and the second component using a tensioning system such that the first component applies a first force to the person's body and the second component applies a second force to the person's body, the first force being generally opposed to the second force, whereby a portion of the person's body is compressed between the first component and the second component;
    (c) wherein the tensioning system includes a rotary closure device operable to selectively draw the first component and the second component together; and
    (d) wherein the first and second components are at least semirigid and have limited pressuring engagement with the person's body when the first and second components are drawn together, the first and second components engaging and applying substantial pressure to the person's body proximate respective middle portions of the first and second components but not proximate opposing ends of the first and second components.

32. The method of claim 31, wherein the tensioning system includes a releasable and adjustable rotary device comprises a housing within which is incrementally drawn a portion of a tensioning line upon selective rotation of a control knob such that the first component and the second component are drawn together.

33. The method of claim 32, further comprising mechanically releasing the tensioning line such that a portion of the tensioning line may be withdrawn from the housing.

34. The method of claim 31, wherein said step (a) comprises positioning the first and second components on opposite sides of a person's arm.

35. The method of claim 34, wherein performance of said step (b) effects side-to-side tissue compression of the arm but does not result in circumferential forces being applied about the arm so as to interfere with blood circulation through the arm.

36. The method of claim 35, wherein the first and second components are positioned on opposite sides of a person's arm proximal the elbow.

37. The method of claim 35, wherein the first and second components are positioned on opposite sides of a person's arm proximal the shoulder.

38. The method of claim 31, wherein said step (a) comprises positioning the first and second components on opposite sides of a person's leg.

* * * * *

UNITED STATES PATENT AND TRADEMARK OFFICE
CERTIFICATE OF CORRECTION

PATENT NO. : 7,618,386 B2
APPLICATION NO. : 11/187590
DATED : November 17, 2009
INVENTOR(S) : Nordt, III et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 550 days.

Signed and Sealed this

Twenty-sixth Day of October, 2010

David J. Kappos
*Director of the United States Patent and Trademark Office*